(12) United States Patent
Cinal (10) Patent No.: US 11,116,662 B2
(45) Date of Patent: Sep. 14, 2021

(54) GLAUCOMA PUMP IMPLANT WORKING BY MEANS OF IRIS MOVEMENTS TO REDUCE INTRAOCULAR PRESSURE

(71) Applicant: Adnan Cinal, Ankara (FR)

(72) Inventor: Adnan Cinal, Ankara (FR)

(*) Notice: Subject to any disclaimer, the term of this patent is extended or adjusted under 35 U.S.C. 154(b) by 204 days.

(21) Appl. No.: 16/302,605

(22) PCT Filed: May 25, 2017

(86) PCT No.: PCT/TR2017/050219
§ 371 (c)(1),
(2) Date: Nov. 16, 2018

(87) PCT Pub. No.: WO2017/209717
PCT Pub. Date: Dec. 7, 2017

(65) Prior Publication Data
US 2019/0201240 A1      Jul. 4, 2019

(30) Foreign Application Priority Data

May 31, 2016   (TR) .................................. 2016/07277

(51) Int. Cl.
*A61F 9/007*            (2006.01)
(52) U.S. Cl.
CPC ................................ *A61F 9/00781* (2013.01)

(58) Field of Classification Search
CPC .......................... A61F 9/00781; A61F 9/0017
See application file for complete search history.

(56) References Cited

U.S. PATENT DOCUMENTS

| 8,038,684 B2 * | 10/2011 | Yaguchi | A61F 9/007 606/107 |
| 2004/0193262 A1 * | 9/2004 | Shadduck | A61F 9/00781 623/4.1 |
| 2005/0049578 A1 * | 3/2005 | Tu | A61B 3/16 604/890.1 |

OTHER PUBLICATIONS

ISR and opinion, dated Jan. 26, 2018.

* cited by examiner

*Primary Examiner* — Ariana Zimbouski
(74) *Attorney, Agent, or Firm* — Crose Law LLC; Bradley D. Crose (57) ABSTRACT

The invention relates to glaucoma pump implant (100) developed for use in reducing intra ocular pressure of glaucoma patients. The invention particularly relates to a glaucoma pump implant (100) that allows the glaucoma pump implant (100) to act as an active pump by utilizing diameter changes of pupil (210) and iris (220) caused by light variations.

1 Claim, 7 Drawing Sheets

GLAUCOMA PUMP IMPLANT WORKING BY MEANS OF IRIS MOVEMENTS TO REDUCE INTRAOCULAR PRESSURE

FIELD OF THE INVENTION

The invention relates to glaucoma pump implant developed for use in reducing intraocular pressure of glaucoma patients.

The invention particularly relates to a glaucoma implant that allows the implant to act as an active pump by utilizing diameter change of pupil and iris caused by light variations.

BACKGROUND OF THE INVENTION

Glaucoma which is known as "Eye Pressure" or "Blackwater Disease" colloquially, is the damage of the visual nerve due to frequent increase of intraocular pressure. As a result of that, the visual field of the person slowly becomes narrower. Glaucoma, a disease that makes itself recognize in the latest stages of the disease, causes severe untreatable damages to the visual nerve when it is late-diagnosed. Intraocular pressure of the eye increases depending on the inability of the intraocular fluid to be released which is produced in the eye and necessary for eye feeding, and the rising intraocular pressure damages the visual nerve cells.

After the diagnosis of glaucoma is made, the aim of the treatment is to stop the damage of the eye nerve by reducing the eye tension and to prevent the progress of the vision loss. Methods that can be applied for that purpose can be divided into three as drug treatment, laser treatment and surgical treatment. Although the first method chosen after diagnosis is usually drug treatment, and despite laser therapy or surgical treatment methods are applied to patients who do not respond adequately to the drug treatment, direct laser interventions or surgical methods can be used especially in cases where diagnosis is late or continuous drug use is not appropriate. In many cases drug treatment is inadequate to stop the progression of the disease. In this case, surgical intervention is applied as the only option.

Types of surgical treatments according to the degree of developmental anomaly of the trabecular meshwork and the transparency of the cornea

- Goniotomy
- Trabeculotomy
- Trabeculectomy
- Tube implantation

Surgeries are performed.

Goniotomy;

Is usually the surgical method of first choice in developmental glaucoma in children. With the aid of a very thin knife, laceration is performed on the filtration system by entering anterior chamber. This process is carried out developmentally to open closed channels. Other surgical methods (trabeculectomy) can be applied to create new drainage channels when it is impossible to intervene the channel again from inside.

Trabeculotomy;

In this surgical method, it is entered into the Canal of Schlemm which is an important collector canal by means of a very thin tool (probe). By means of that tool, it is entered into anterior chamber and a new drainage path is created. This method is preferred in some glaucoma types or when the cornea is not as transparent as for the Goniotomy to be performed.

Trabeculectomy;

There is sclera and conjunctival tissue covering it in the strong frontal wall of the eye. New drainage channels are created in the eye with that method. Usually, the flap (tissue cover) is created surgically near the area under the upper lid. 3×1 mm tissue is removed under the flap and entering anterior chamber.

Then this flap is re-stitched with fine sutures and it is covered with the conjunctiva which is the front layer of the eye. The intraocular fluid flows under the conjunctiva through this channel formed and is then removed with blood vessels from there.

Tube Implantation;

Specially designed tubes are used for intraocular fluid excretion. This method is preferred in cases when other methods, e.g. the flap formed with trabeculectomy, are inadequate.

In glaucoma treatments, all operations performed and implants used are operated with a hydrostatic pressure differential and a passive mechanism. In this case, occlusion occurs in the implants over time and when the pressure is similar on both sides of the globe, intraocular pressure does not decrease and it becomes a necessity to repeat the operation.

Despite all the above-mentioned treatment methods, both treatments are inadequate and very serious side effects of the treatments applied to the patients are emerging in many cases. For this reason, new researches for glaucoma treatment are carried out rapidly all over the world.

After preliminary research about the state of the art, the patent document numbered "2013/11729" has been examined. In the summary part of the invention subjected to application the following information is given: "C-shaped cross-section latex tube implant for reduction of intraocular pressure. A proximal end serves as a conduit for aqueous humor to bypass angle structures in the eye. A distal end serves as a nidus for the patient's cells to form a capsule on. Inflation of the cellular capsule forms a tube for conduction of aqueous humor and filters this fluid into the extracellular space under the conjunctiva. A series of lateral portions of the distal tube are removed. A ligature is tied to each of the remaining whole cylindrical portions whereby flow through the whole cylindrical portions is prevented. An anchor comprises a split end of the tube wherein the end of the tube is split multiple times such as a bifurcation. The nidus comprises a portion extending outwardly from the exposed interior of the tube. This portion has a cross section in the form of a wavy closed. The method comprises the steps of implanting the distal portion of the cylindrical tube under the conjunctiva and anchoring the distal end of the cylindrical tube to the sclera at the limbus; inserting the proximal, intact end of the tube into the anterior chamber through a needle track; ligating the proximal end to prevent hypotony; waiting about a week for a capsule to grow around the tube; and, releasing a ligature around the proximal end after about a week to inflate a bleb; measuring the intraocular pressure to determine whether additional drainage is required or not; if additional drainage is required, releasing ligature(s) in order that additional blebs are inflated." That technique works with the passive hydrostatic mechanism as mentioned above and has the common disadvantages of all passive systems.

After preliminary research about the state of the art, the patent document numbered "WO2014131423" has been examined. In the invention subjected to the application, it is also mentioned about an implant with passive mechanism developed with the aim of reducing eye pressure.

In conclusion, all the methods and implants developed in glaucoma treatment so far are based on the idea that aqueous humour leaves the eye with a passive hydrostatic pressure differential mechanism. There is not yet an implant design that pumps out the intraocular aqueous humour actively. In these cases, either the drainage tubes are clogged or the drainage process is stopped when the pressure on the side to which the liquid is drained is increased. This situation often results in inadequacy in reducing the intraocular pressure. Accordingly, due to the inadequacy of the existing solutions in treatment, it has become necessary to make an improvement in the respective technical field.

In recent studies, it has been observed that some fibers from the iris tissue in the eye stick to the trabecular meshwork in some people and that the mechanical force of the iris pulls back and forth over the trabecular meshwork by the dilation and constriction of the pupil under different light conditions. It has been asserted that this pulling action acts as a pump and that it increases the outflow of the intraocular aqueous humour. It is also known that contraction of the corpus ciliare, which adapt the eye lens, also stretches the trabecular meshwork and increases the outflow of the intraocular aqueous humour by enlarging the holes on the trabecular meshwork. It is also known that the intraocular pressure is thus effectively reduced by the increase of fluid flow. What is more, the substance called pilocarpine has been used for many years to reduce the intraocular pressure by this mechanism.

BRIEF SUMMARY OF THE INVENTION

The most important object of the invention is that the implant acts as an active pump by the motion of the trabecular meshwork back and forth by means of that normally naturally existing iris pump mechanism utilizes the diameter change of the pupil, and thus ensures the removal of the intraocular aqueous humour with the aid of the natural mechanism just like the iris protrusions, and provides that the eye pressure decreases.

A further important object of the invention is to increase the outflow of the intraocular aqueous humour and to reduce the intraocular pressure in this way by expanding the holes of the trabecular mesh on the time intervals when the iris contracts, just like the corpus ciliare muscle, with the help of the implant.

Another important object of the invention is to prevent the vision loss of the patient by reducing the intraocular pressure independent of the hydrostatic pressure difference.

Another object of the invention is to prevent the problem of clogging by acting as an active pump and not opening any channel.

One of the objects of the invention is that the string allows movement of the pupil by being made from a flexible material and to prevent the breakage of the implant.

Another object of the invention is that the implant prevents the automatically collapsing and clogging of the canal of Schlemm into which the implant is placed because of the zigzagging form of the implant.

One of the objects of the invention is that the implant is brought into use in a symmetrically folded manner in the cartridge. Thus, placement stage of the implant is facilitated.

Structural and characteristic specifications and all advantages of the invention will be understood more clearly by means of figures given below, and detailed descriptions written by referencing to those figures. Therefore, assessment should be done by taking these figures and detailed description into consideration.

REFERENCE NUMBERS

100. Glaucoma Pump Implant
110. Implant Abutment
120. String
130. Hook
200. Eye
210. Pupil
220. Iris
230. Cornea
240. Canal of Schlemm
250. Anterior Chamber
260. Eye Lens
300. Implantation Injector

DETAILED DESCRIPTION OF THE INVENTION

The pump mechanism of the glaucoma pump implant (100) that is subject of the invention is operated by three different mechanisms:

a. The trabecular meshwork constitutes a negative pressure (vacuum) in the Canal of Schlemm (240) when it is pulled forward rapidly with the aid of the glaucoma pump implant (100) and with the power of the iris (220). This vacuum force increases the passage of liquid from the anterior chamber (250) at which the pressure is high to the Canal of Schlemm (240).

b. When the trabecular meshwork is pulled forward with the aid of the glaucoma pump implant (100) and with the power of the iris (220), the holes, allowing one-way passage of the liquid on the trabecular mesh, allow more fluid to pass through the Canal of Schlemm (240) by expanding.

c. When the iris (220) is again constricted, the unidirectional permeable trabecular meshwork returns to its original position and applies pressure to the fluid-filled Canal of Schlemm (240), and allows more fluid to flow from the Canal of Schlemm (240) to the discharging ducts called collecting ducts.

There is a liquid circulating to feed the tissues in the eye (200), in the anterior chamber (250). This liquid is produced in the eye (200). It is ejected out of the eye (200) through another group of canals. This fluid cannot be ejected out because of the blockage of the tissue (trabecular meshwork) channels between the Canal of Schlemm (240) and the interior of the eye (200) in some eyes (200), and thus the pressure inside the eye (200) is increased.

The invention developed to reduce the rising pressure inside the eye (200) is a glaucoma pump implant (100) having a "T" shape one end of which is mounted on iris (220) and one end of which is positioned on the canal of Schlemm (240) by piercing the trabecular mesh. This glaucoma pump (100) ensures that the intra ocular fluid is sent out of the eye (200) both by expanding the holes on the trabecular mesh and by active pumping thereby pulling forward dropping cribriform spongy trabeculae via the movements of the iris (220). Because the trabecular meshwork (200) permits passage of the fluid only one way and into the Canal of Schlemm (240), it will carry the trabeculae fluid into the one-way Canal of Schlemm (240) by the movements of glaucoma pump implant (100). The hook (130) located at the lower end of the string (120) that is the vertical portion of the glaucoma pump implant (100) is fixed to the iris (220) while the implant abutment (110) which is the horizontal portion shall remain within the Canal of Schlemm (240).

The glaucoma pump implant (100) that is subject of the invention has been developed for use in reducing the intraocular eye (200) pressure of glaucoma patients. In the most general form the invention comprises; An implant abutment (110) that ensures both expanding of the trabecular holes by pulling forward and dropping the trabeculae and sending the intra eye (200) fluid out of the eye (200) by active pumping; string (120) which transmits the tensile force generated by constriction of the pupil (210) to the implant abutment (110), hook (130) that is positioned at the end portion of the string (120), and ensures that the string (120) is connected to the iris (220).

After implanting the glaucoma pump implant (100) into the eye (200), the pupil (210) which is a space in the middle of the iris (220) is dilated or constricted in various light conditions in daily life, and this change of the pupil (210) causes the iris (220) to move. This movement of the iris (220) stretches the string (120), and the stretched string (120) pulls and drops the implant abutment (110) which remain in the Canal of Schlemm (240). That leads to enlargement of the holes which are on the trabecular meshwork and allow the liquid to exit uni-directionally out of the eye (200), thereby to the increase of the outflow of the fluid. By the aid of this natural mechanical process, the intra ocular fluid is pumped out of the eye (200) via the trabecular meshwork and the Canal of Schlemm (240). Thus, the pressure in the eye (200) is reduced.

Figure 1:
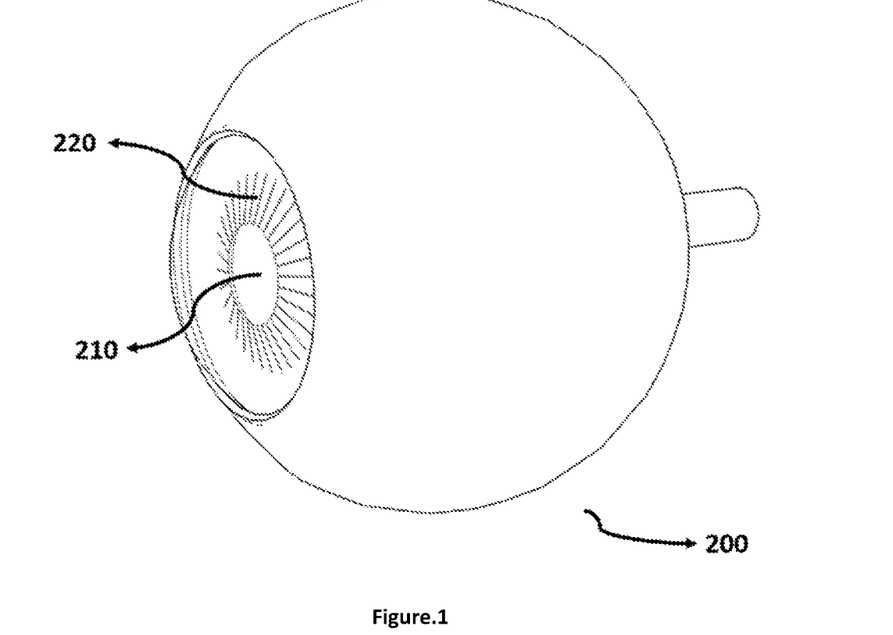
FIG. 1; The illustration showing the general perspective of the eye.
Figure 2:
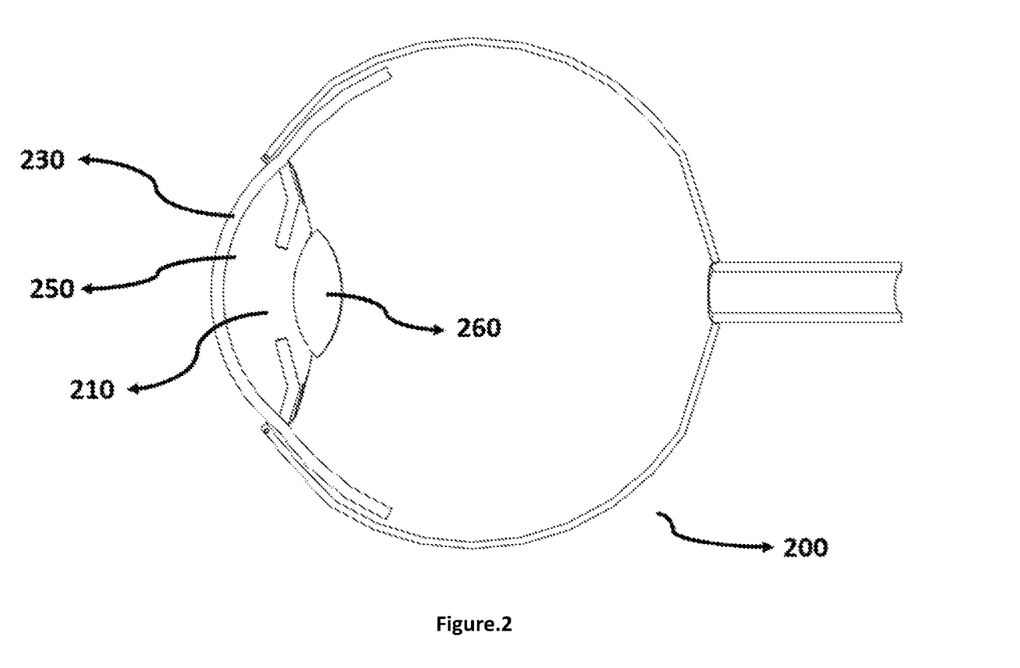
FIG. 2; The illustration showing the cross section view of the eye.
Figure 3:
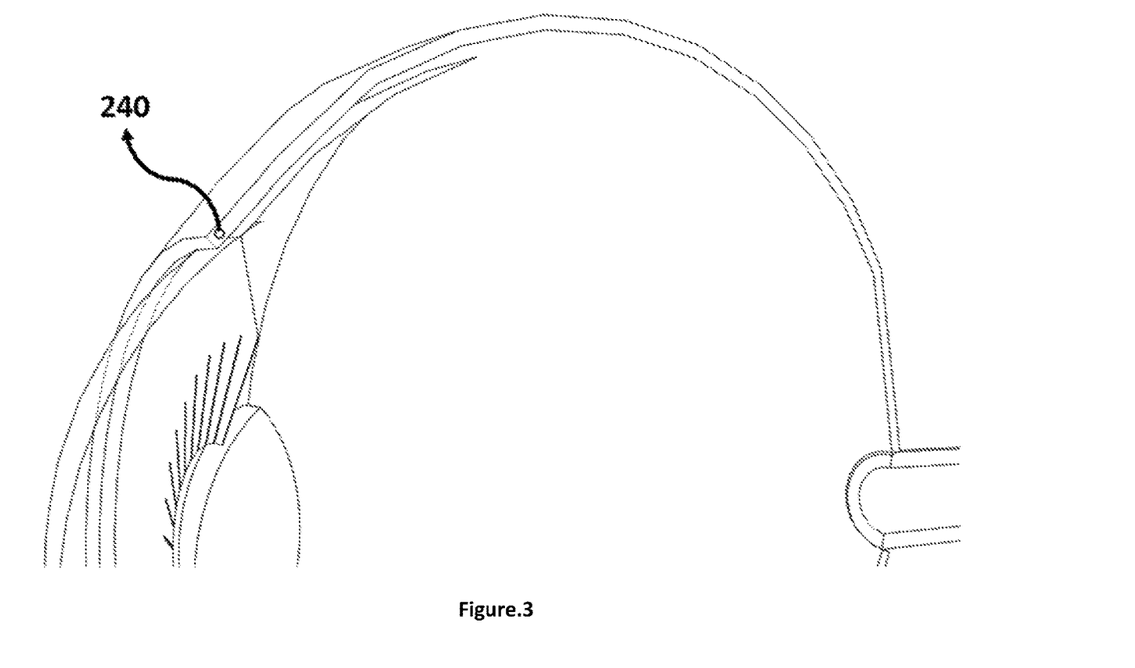
FIG. 3; The illustration showing the cross perspective section view of the eye.

The images of the eye (200) in different angles and the pupil (210), the iris (220), the cornea (230), the eye lens (260), and the anterior chamber (250) are shown in FIG. 1, FIG. 2. In FIG. 3, Canal of Schlemm (240), in which the implant abutment (110) which is the component of the glaucoma pump implant (100) that is subject of the invention will be placed, is shown.

Figure 4:
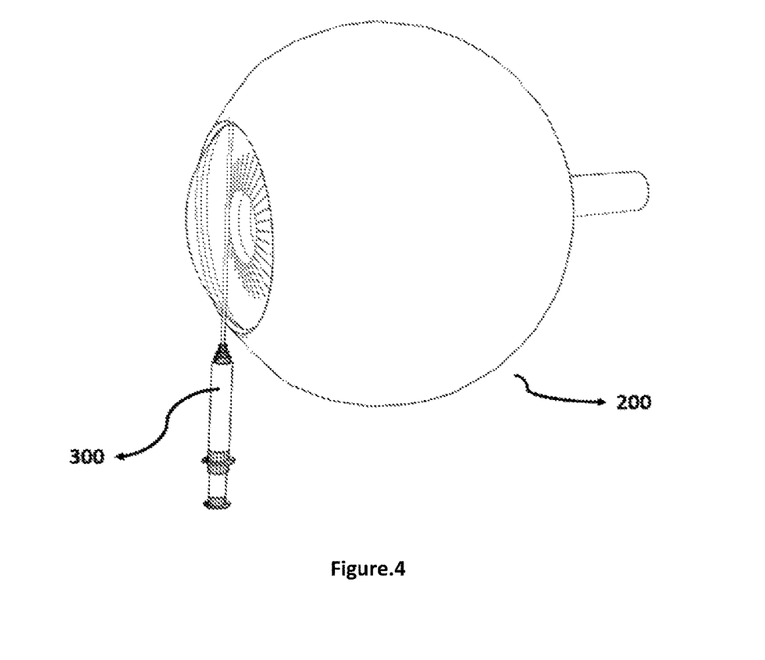
FIG. 4; The illustration showing the injection of the implant that is subject of the invention.

The glaucoma pump implant (100) that is subject of the invention is inserted into the Canal of Schlemm (240) by drilling the trabecular meshwork of the implant abutment (110) with the help of an implantation injector (300) through the anterior chamber (250), passing the cornea (230) as shown in FIG. 4. Then the hook (130) at the end of the string (120) ensures that the glaucoma pump implant (100) is fixed by compressing the iris (220). That hook (130) may be positioned at the rear of the iris (220) as well as it may be positioned to iris (220) from the visible side. Thus, if desired, the hook (130) will not be visible and there will be no indication of operation since the string (120) is transparent.

Figure 5:
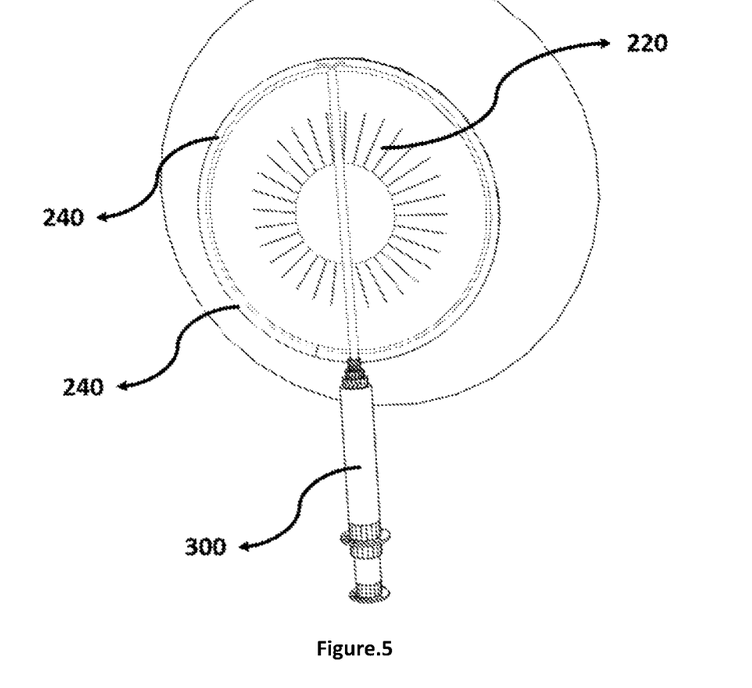
FIG. 5; The illustration showing the injection of the implant that is subject of the invention as the canal of Schlemm in opened manner.
Figure 6:
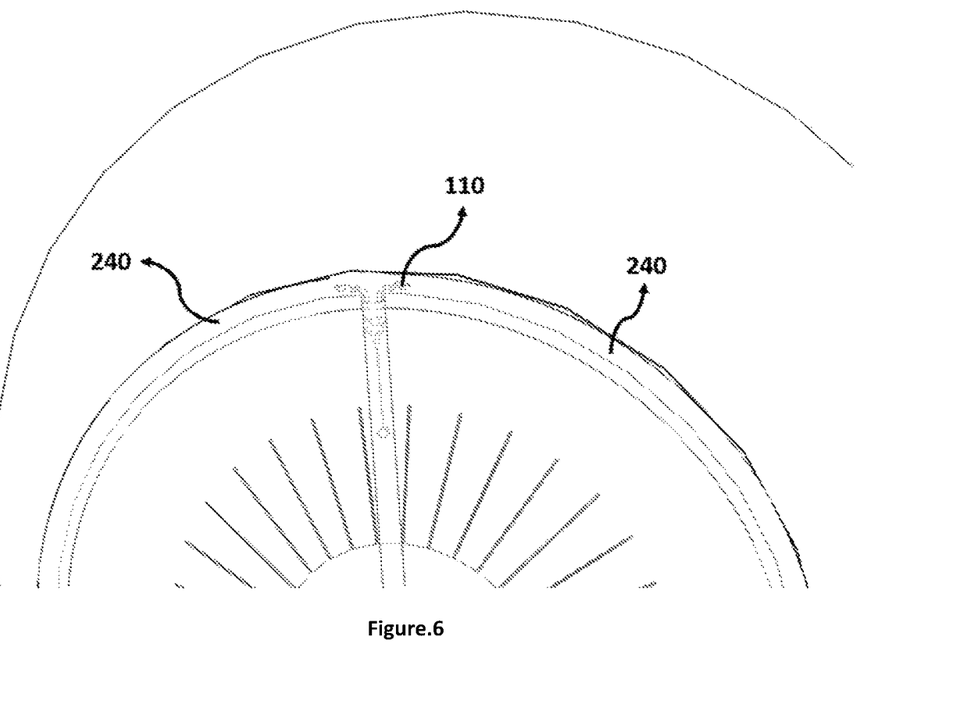
FIG. 6; The detailed sectional illustration showing the injection step of the implant that is subject of the invention as the canal of Schlemm in opened manner.
Figure 7:
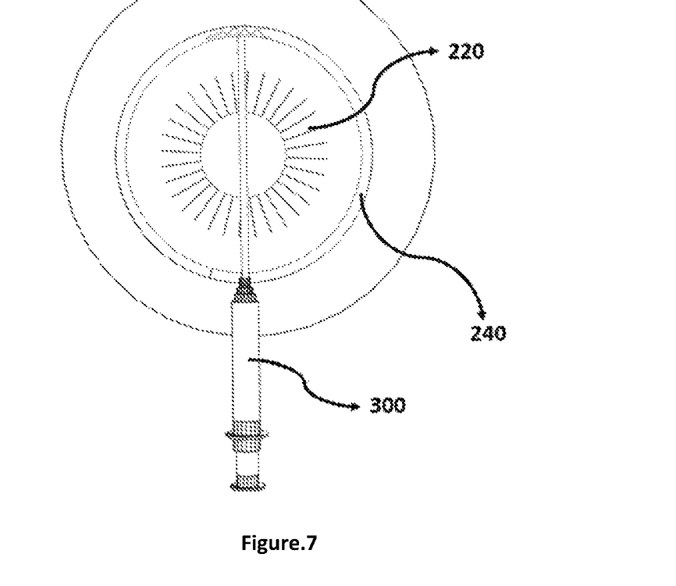
FIG. 7; The perspective illustration showing the injection step of the implant that is subject of the invention as the canal of Schlemm in opened manner.
Figure 12:
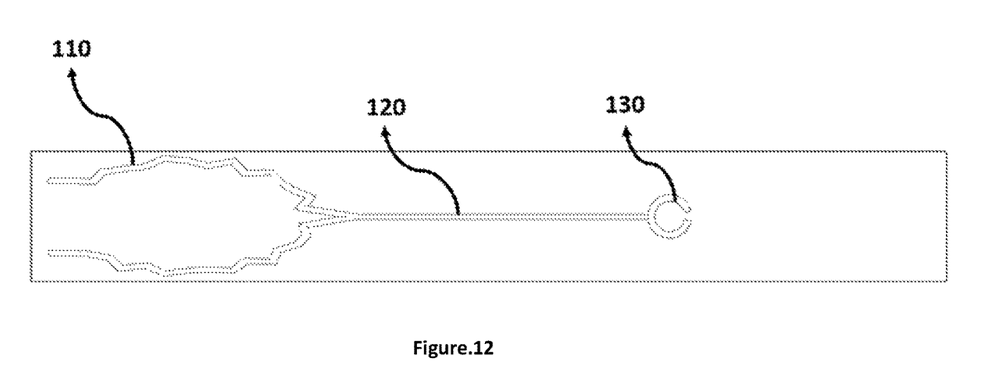
FIG. 12; The illustration showing the view of the position of the implant that is subject of the invention in the injector.

The glaucoma pump implant (100) comes as folded in the implantation injector (300) as shown in FIG. 12. It is implanted to the eye (200) as shown in FIG. 5, FIG. 6, FIG. 7, by opening as pushed inwardly to Canal of Schlemm (240).

Figure 8:
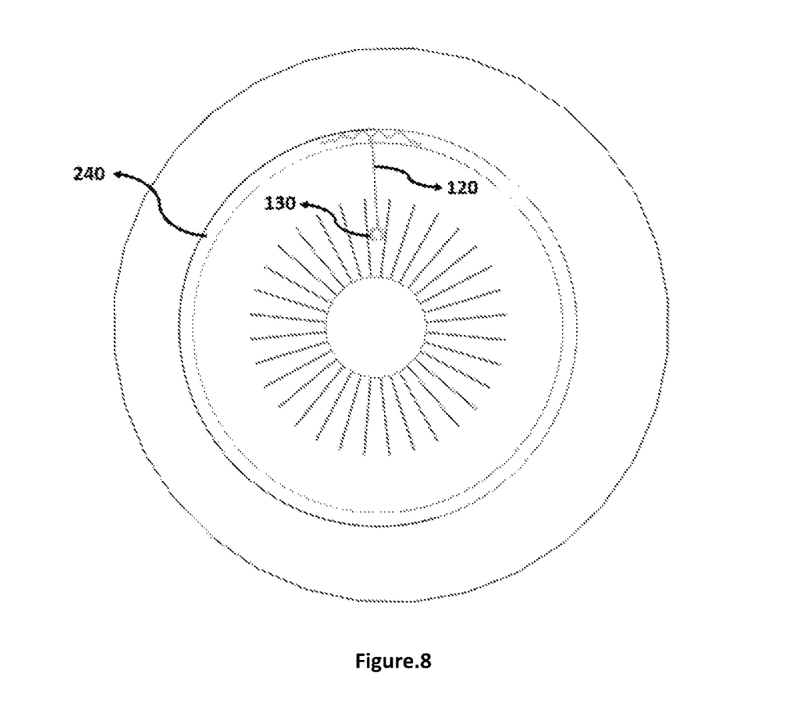
FIG. 8; The perspective illustration showing the location of the implant that is subject of the invention after it is placed to the eye as the canal of Schlemm in opened manner.
Figure 9:
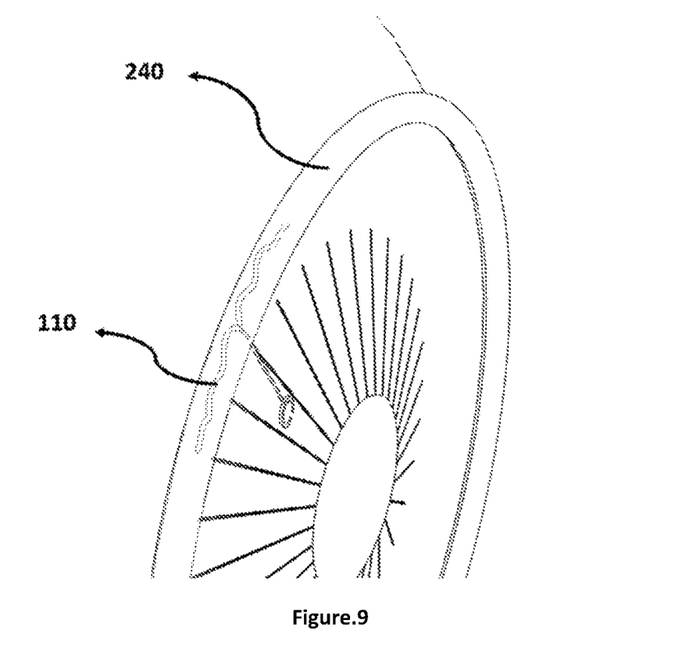
FIG. 9; The detailed sectional illustration showing the location of the implant that is subject of the invention after it is placed to the eye as the canal of Schlemm in opened manner.
Figure 10:
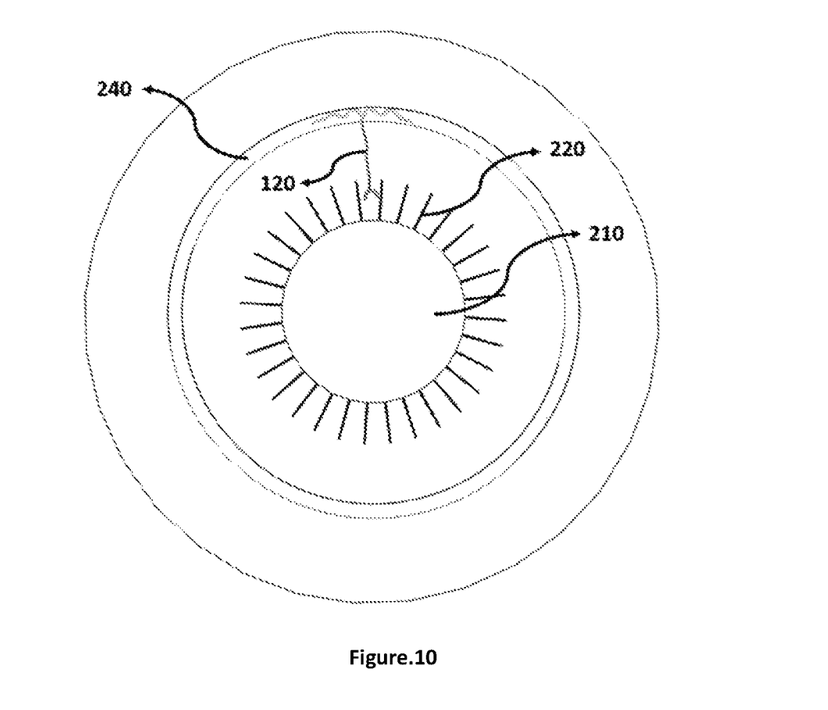
FIG. 10; The perspective sectional illustration showing the pupil's enlargement state location of the implant that is subject of the invention after it is placed to the eye as the canal of Schlemm in opened manner.
Figure 11:
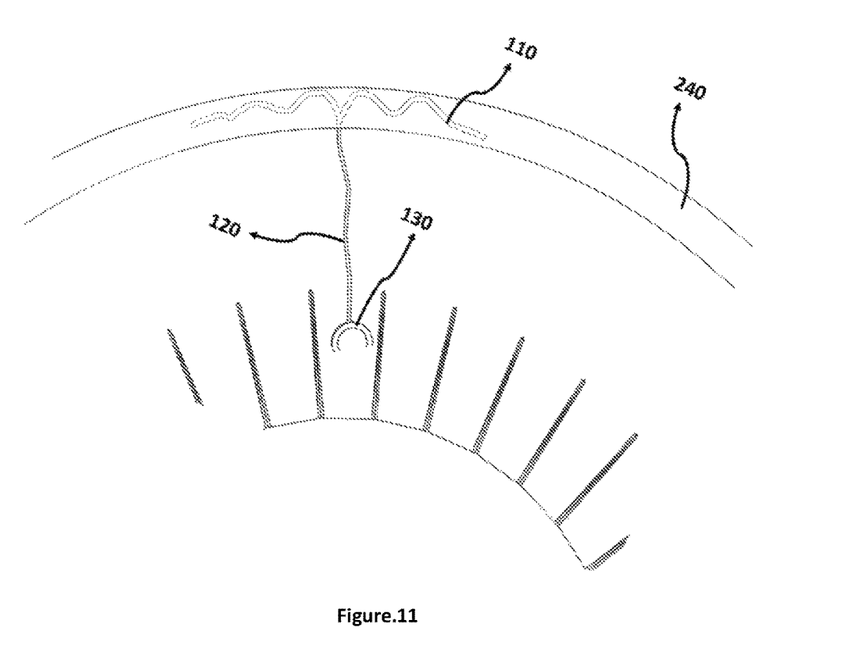
FIG. 11; The detailed sectional illustration showing the pupil's enlargement state location of the implant that is subject of the invention after it is placed to the eye as the canal of Schlemm in opened manner.

After the implantation, the active pump mechanism works by changing of the diameter of the pupil (210). As shown in FIG. 8 and FIG. 9, the iris (220) is enlarged when the pupil (210) is constructed in the luminous environment and the string (120) is stretched. By the tension of the string (120), the string (120) pulls the implant abutment (110) toward itself. Thus, the trabeculae are pulled forward. The pupil (210) is dilated and loosen the string (120), as shown in FIG. 10 and FIG. 11, after the dilation of the pupil (210) again as a result of reduction in the amount of light. With the loosening of the string (120), the string (120) releases the implant abutment (110) which it previously pulled towards itself. Thus, it is ensured that trabeculae goes back to its former position.

Because high pressure in anterior chamber than canal of Schlemm and the trabecular meshwork (200) permits passage of the fluid only one way and into the Canal of Schlemm (240), it will carry the trabeculae fluid into the one way Canal of Schlemm (240) by the movements of glaucoma pump implant (100).

The change in diameter of the pupil (210) due to the differences of light conditions causes the trabeculae to be continuously pulled with the help of the glaucoma pump implant (100) so that the liquid in the eye (200) is sent out of the eye (200) and therefore the pressure in the eye (200) is reduced.

Figure 13:
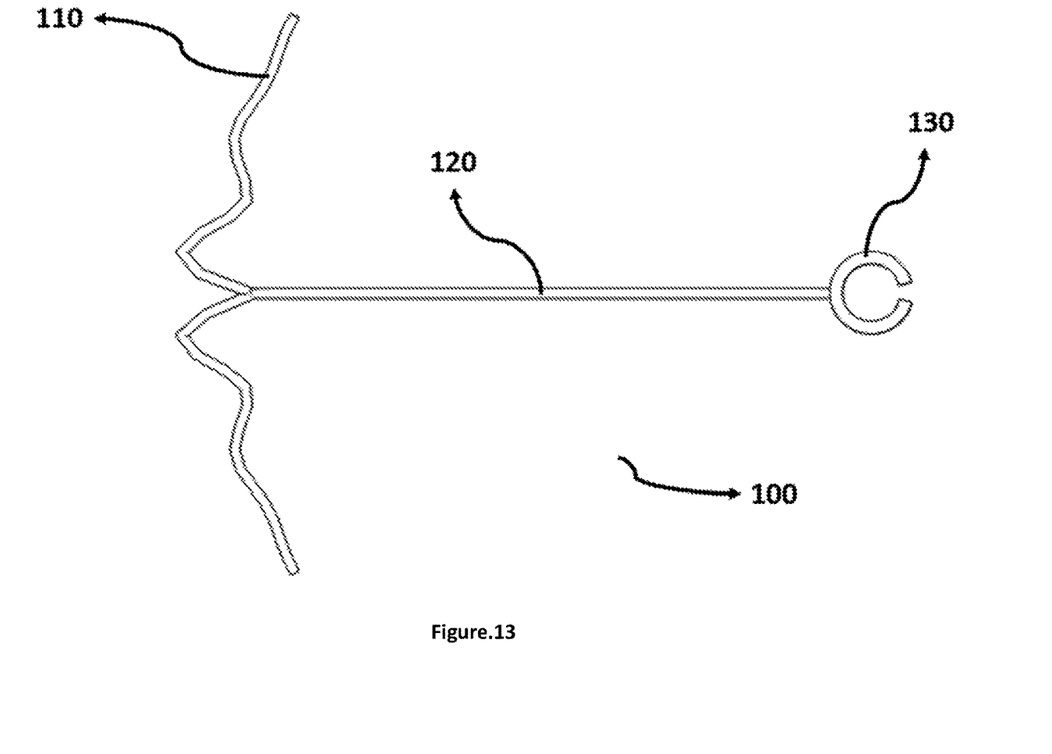
FIG. 13; The illustration showing the stretched view of the string after the implant that is subject of the invention is placed to the eye.
Figure 14:
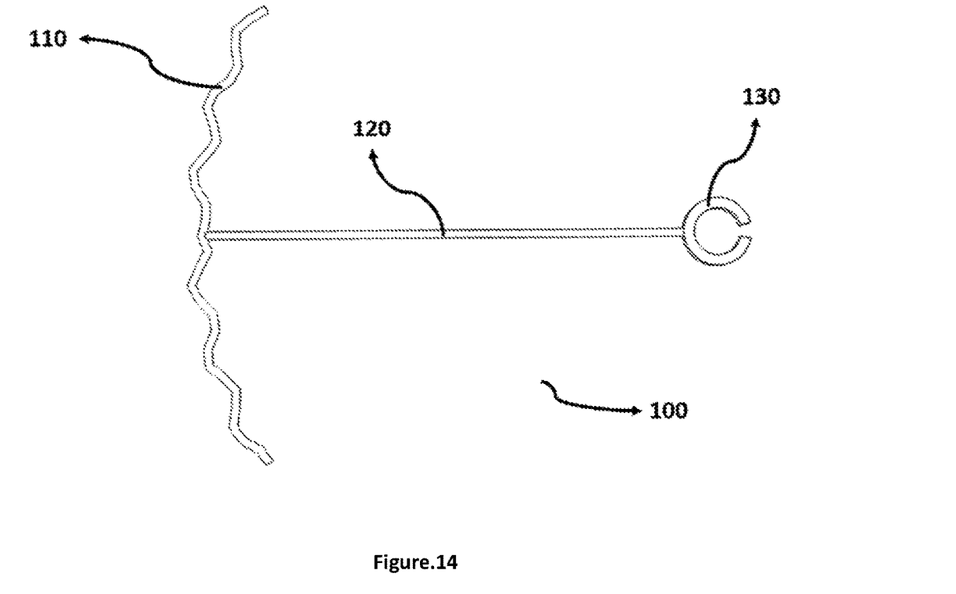
FIG. 14; The illustration showing the view in different form of the implant that is subject of the invention.

The glaucoma pump implant (100) is manufactured from biocompatible material. Furthermore, the glaucoma pump implant (100) is presented to the user in the implantation injector (300). In this way, both the hygiene will be ensured and the doctor will not waste time placing the glaucoma pump implant (100) in the implantation injector (300). The glaucoma pump implant (100) is placed in the implantation injector (300) as shown in FIG. 13. In this position, the implant abutment (110) is folded and the string (120) is positioned in a flexible manner so as not to be broken in the case of excessive tension. Its position after the implantation process to the eye (200) is shown in FIG. 13. Furthermore, the invention can be produced in different forms as shown in FIG. 14.

The glaucoma pump implant (100) that is subject of the invention is in zigzag structure to prevent the implant abutment (110) from collapsing and blocking the Canal of Schlemm (240) per se. Moreover, the implant abutment (110) is inclined in the horizontal plane so that the implant abutment (110) can adapt to the circumference of the Canal of Schlemm (240). The said string (120) is also in flexible structure in order to prevent the string (120) from breaking when the pupil (210) is constricted and that the string (120) can be stretched.

The invention claimed is:

1. A glaucoma pump implant (100) for use in reduction of intraocular pressure in glaucoma patients characterized in that the glaucoma pump implant (100) comprises;
- an implant abutment (110) that is configured to ensure both expanding of trabecular holes and trabeculae, which is inclined in a horizontal plane so that the implant abutment (110) can adapt to a circumference of canal of Schlemm (240) and which has a zigzag structure to prevent the implant abutment (110) from blocking a canal of Schlemm (240),
- a string (120) configured to transmit a tensile force, which is a flexible structure in order to prevent the string (120) from breaking when a pupil (210) is constricted or dilated, and
- a hook (130) configured to ensure that the string (120) is connected to an iris (220).

* * * * *